United States Patent
Menyes et al.

(10) Patent No.: US 6,696,615 B1
(45) Date of Patent: Feb. 24, 2004

(54) METHOD OF SEPARATING POLYCYCLIC AROMATIC HYDROCARBONS BY MEANS OF CHROMATOGRAPHY

(76) Inventors: Ulf Menyes, Stefanistrasse 6, D-17489 Griefswald (DE); Ulrich Roth, Dorfstrasse 13a, D-17498 Levenhagen (DE); Thomas Jira, Joelkenbergring 26, D-17498 Potthagen (DE)

(*) Notice: Subject to any disclaimer, the term of this patent is extended or adjusted under 35 U.S.C. 154(b) by 215 days.

(21) Appl. No.: 09/295,539

(22) Filed: Apr. 21, 1999

(30) Foreign Application Priority Data

Apr. 21, 1998 (DE) .......................... 198 35 604

(51) Int. Cl.$^7$ ................................. C07C 7/12
(52) U.S. Cl. ................. 585/825; 585/830; 585/831
(58) Field of Search ................. 585/825, 830, 585/831

(56) References Cited

U.S. PATENT DOCUMENTS

| | | | | |
|---|---|---|---|---|
| 5,143,784 A | * | 9/1992 | Mita | .......................... 426/336 |
| 6,093,517 A | * | 7/2000 | Ito et al. | .................. 430/270.1 |

FOREIGN PATENT DOCUMENTS

| | | |
|---|---|---|
| EP | 0 786 661 A2 | 1/1997 |
| JP | 411302202 A | * 11/1999 |
| JP | 411326306 A | * 11/1999 |
| WO | WO 97/37995 | 10/1997 |

OTHER PUBLICATIONS

Brindle, Roland et al., Journal of *Chromatography A*, 731 (1996) pp. 41–46 Siclica–bonded calixarenes in chromatography I. Synthesis and characterization by solid–state NMR spectroscopy.

Xu, W. et al., *Chromatographia*, vol. 48, No. 3/4 (Aug. 1998) pp. 245–250 "Preparation and Characterization of p–tert–Butyl–Calix[6]arene–Bonded Silica Gel Stationary Phase for High Performance Liquid Chromatography".

Chemical Abstracts, vol. 128, No. 16, Apr. 20, 1998, S. Zhang et al., "Gas chromatography of calix[4]arene derivatives".

Chemical Abstracts, vol. 129, No. 23, Dec. 7, 1998, Z. Zheng et al., "Two kinds of calix [4] arene derivatives as capillary gas chromatography stationary phases".

Sun, S. et al., *Anal. Chem.*, 69 (3) (1997) pp. 344–348 "Capillary electrokinetic chromatography employing p–(Carboxyethyl) calix[n] arenes as runnning buffer additives".

Kalchenenko, O.I. et al, *Journal of Chromatographic Science*, vol. 36 (May 1998) "Effect of Octakis (diethoxyphosphoryloxy) –tert–butyl–calix[8] arene in mobile phase on the reversed–phase retention behavior of aromatic compounds: Host–guest complex formation and Stability Constants Determination".

\* cited by examiner

*Primary Examiner*—Glenn Caldarola
*Assistant Examiner*—Tam M. Nguyen
(74) *Attorney, Agent, or Firm*—Scully, Scott, Murphy & Presser

(57) ABSTRACT

The invention relates to an effective method of separating polycyclic aromatic hydrocarbons by means of a chromatographic separation method. This is achieved by using, according to the invention, calixarene-modified separation phases as stationary phase for chromatography in order to separate polycyclic aromatic hydrocarbons. The calixarene-modified stationary phases are particularly suitable for separating polycyclic aromatic hydrocarbons in liquid chromatography separation methods.

3 Claims, No Drawings

METHOD OF SEPARATING POLYCYCLIC AROMATIC HYDROCARBONS BY MEANS OF CHROMATOGRAPHY

The invention relates to a method of separating polycyclic aromatic hydrocarbons by means of chromatographic methods.

Since some of the polycyclic aromatic hydrocarbons are carcinogenic and thus count as environmental poisons, they have to be analyzed in soil and water.

Previous methods determine the polycyclic aromatic hydrocarbons with the aid of nonpolar chromatography phases, for example RP-C18 phases. Standard methods are known for this purpose, as are prescribed, for example, in the drinking water regulations of the Federal Republic of Germany or in the analytical method EPA 610 of the Environmental Protection Agency of the United States of America.

Furthermore, Shaowen, Z et al.: Gas chromatography of calix[4]arene derivatives; published in: Fenxi Kexue Xuebao (1998), 14 (1), pp. 14–18, studied gas chromatographic phases comprising two different calix[4]arenes and their interaction with the polycyclic aromatic hydrocarbons and similar systems. The authors assume that the latter form host-guest compounds with the calix[4]arenes.

According to Sun, S., Gutsche, D. et al.: Capillary electrokinetic chromatography employing p-(Carboxyethyl) calix[n]arenes as running buffer additives; published in: Anal. Chem. (1997), 69 (3), pp. 344–348 and Kalchenko, O. I. et al.: Effect of Octakis(diethoxyphosphoryloxy)-tert-butylcalix[8]arene in mobile phase on the reversed-phase retention behavior of aromatic compounds: host-guest complex formation and stability constants determination; published in: Journal of Chromatographic Science, Vol. 36, May 1998, similar host-guest compounds are described when using calixarenes in capillary electrophoresis (CE) and in high performance liquid chromatography (HPLC) with, according to the method, the calixarenes being used as an Additive to the eluant.

The object of the invention is an effective separation of polycyclic aromatic hydrocarbons by means of chromatographic methods.

According to the invention, this object is achieved by using the calixarene-modified stationary separation phase for separating the polycyclic aromatic hydrocarbons by means of chromatography. For this purpose, the polycyclic aromatic hydrocarbons are dissolved in a suitable solvent, or solutions of polycyclic aromatic hydrocarbons in a liquid medium can be used.

The samples of the dissolved polycyclic aromatic hydrocarbons are passed with the aid of a suitable eluant in the form of a solvent and/or solvent mixture over the calixarene-modified stationary separation phase, with the polycyclic aromatic hydrocarbons being spatially separated from one another. The separated substances are then detected.

The examples illustrate the invention.

EXAMPLE 1

A mixture of benzene, naphthalene and anthracene is separated by means of an HPLC unit provided with a ternary gradient system and a UV detector using a Caltrex A I column having dimensions of 25 cm×4.6 mm. The eluant used is a mixture of acetonitrile/methanol/water in a ratio of 1:3:6 (v/v/v) at a flow rate of 1 ml/min. The detector wavelength is 254 nm.

The following separation result is achieved:

| Substance | Time (min) |
|---|---|
| Benzene | 2.1 |
| Naphthalene | 3.2 |
| Anthracene | 5.4 |

EXAMPLE 2

A mixture of phenanthrene, fluoranthene, chrysene and perylene is separated by means of an HPLC unit provided with a ternary gradient system and a UV detector using a Caltrex B I column having dimensions of 25 cm×4.6 mm. The eluant used is a mixture of acetonitrile/methanol/water in a ratio of 1:3:6 (v/v/v) at a flow rate of 1 ml/min. The detector wavelength is 254 nm.

The following separation result is achieved:

| Substance | Time (min) |
|---|---|
| Phenanthrene | 9.7 |
| Fluoranthene | 10.2 |
| Chrysene | 13.9 |
| Perylene | 18.0 |

The liquid chromatography separation method of the invention using calixarene-modified stationary separation phases can be used in thin-layer and thick-layer chromatography, column chromatography such as HPLC, solid phase extraction, supercritical chromatography, for example SCE, electrophoresis, for example CE.

What is claimed is:

1. A method of separating polycyclic aromatic hydrocarbons comprising dissolving polycyclic aromatic hydrocarbons in a solvent wherein a solution is formed; passing said solution over a calixarene-containing stationary separation phase wherein said polycyclic aromatic hydrocarbons are spatially separated from one another.

2. A method in accordance with claim 1 wherein said calixarene-containing stationary separation phase includes silanol or a silanol group.

3. A method in accordance with claim 1 wherein said solution is liquid and said method is liquid chromatography.

* * * * *